United States Patent [19]

Samejima et al.

[11] Patent Number: 4,462,982

[45] Date of Patent: Jul. 31, 1984

[54] MICROCAPSULES AND METHOD OF PREPARING SAME

[75] Inventors: Masayoshi Samejima, Minoh; Goichi Hirata, Yawata; Yoshiyuki Koida, Katano; Yoshinori Kobayashi, Toyonaka; Akira Kida, Settsu, all of Japan

[73] Assignee: Tanabe Seiyaku Co., Ltd., Osaka, Japan

[21] Appl. No.: 419,695

[22] Filed: Sep. 17, 1982

[30] Foreign Application Priority Data

Oct. 5, 1981 [JP] Japan ................................ 56-159285

[51] Int. Cl.³ ........................ B01J 13/02; A61K 9/50; A61K 9/62
[52] U.S. Cl. ................................ 424/35; 428/402.24; 427/213.3; 424/19
[58] Field of Search .................... 252/316; 424/35, 19; 427/213.3; 428/402.24

[56] References Cited

U.S. PATENT DOCUMENTS

| | | | |
|---|---|---|---|
| 3,485,914 | 12/1969 | Corn | 424/22 |
| 3,909,444 | 9/1975 | Anderson | 252/316 |
| 4,205,060 | 5/1980 | Monsimer | 424/35 |
| 4,218,333 | 8/1980 | Samejima | 424/35 |
| 4,252,786 | 2/1981 | Weiss | 424/35 |
| 4,341,759 | 7/1982 | Bogentoft | 424/35 |

FOREIGN PATENT DOCUMENTS 49-100216 9/1974 Japan.
54-119021 9/1979 Japan.

Primary Examiner—Richard D. Lovering
Assistant Examiner—Anne Brookes
Attorney, Agent, or Firm—Jordan B. Bierman; Linda Bierman

[57] ABSTRACT

Ethylcellulose microcapsules, wherein a polymer material which shows at least 1.2 times increase in weight by immersing it in water at 37° C. is incorporated into the ethylcellulose coating walls and/or the core material thereof, are disclosed. Said ethylcellulose microcapsules show rapid release of the core material in digestive organs such as stomach.

17 Claims, No Drawings

MICROCAPSULES AND METHOD OF PREPARING SAME

This invention relates to novel microcapsules and a method of preparing the same.

The release control of a core material from microcapsules has been accomplished thus far by increasing the thickness of the coating walls of said microcapsules or by forming compact coating walls on and around the core material thereof so as to decrese the permeability thereof. However, ethylcellulose has usually been used as a wall-forming material for microcapsules of a medicament in order to mask unpleasant odor or taste thereof; such ethylcellulose microcapsules do not release the active ingredient in the stomach.

As a result of various investigations, we have now found that ethylcellulose microcapsules which are able to protect the core material effectively and, when administered orally, release the core material rapidly in digestive organs such as the stomach, can be readily obtained by incorporating a swellable polymer material, i.e, a polymer material swellable in water, into the ethylcellulose coating walls and/or the core materials of said microcapsules.

According to the present invention, such novel microcapsules can be prepared by the steps of:
(i) dissolving ethylcellulose in cyclohexane,
(ii) dispersing a core material in said solution,
(iii) cooling the dispersion in the presence of said swellable polymer material until ethylcellulose separates out from the dispersion to form coating walls on and around the core material, and
(iv) recovering the resultant microcapsules therefrom.

Alternatively, such microcapsules of the invention may be prepared by the steps of:
(i) dissolving ethylcellulose in cyclohexane,
(ii) dispersing said swellable polymer material-containing core material in said solution,
(iii) cooling the dispersion in the presence or absence of said swellable polymer material until ethylcellulose separates out from the dispersion to form coating walls on and around the core material, and
(iv) recovering the resultant microcapsules therefrom.

Any pharmaceutically active compounds or medicaments which are insoluble or incompatible in cyclohexane or a mixture of cyclohexane and another solvent (e.g., n-hexane can be used as the core material to be microencapsulated in the present invention. Such pharmaceutically active compounds or medicaments to be microencapsulated may be solids, gels, or semi-solids. In order to prepare a homogeneous dispersion at the microencapsulation step, it is preferred that the pharmaceutically active compounds or medicaments have a particle size of about 30 to about 1000$\mu$, especially about 50 to about 500$\mu$. On the other hand, ethylcellulose having an ethoxy content of about 46.5 to about 55 w/w% is preferably used as the wall-forming material of the invention. It is also preferred that the viscosity of said ethylcellulose, when measured at 25° C. with respect to a 5 w/w% solution in toluene-ethanol (4:1), is within the range of about 3 to about 500 cP, especially 40 to 200 cP. A suitable amount of said ethylcellulose to be used is about 0.01 to 10 grams, especially about 0.05 to about 2 grams, per gram of the core material used. If required, the solvent cyclohexane may be used in admixture with another solvent such as n-hexane.

A wide variety of polymer materials which show at least 1.2 times increase in weight when immersed in water at 37° C. can be used as the "polymer material swellable in water" of the present invention. Representative examples of such polymer material include starch; crystalline cellulose; agar; alginic acid or its alkaline earth metal salt; hydroxy-lower alkyl-polysaccharide carboxy-lower alkyl-polysaccharide or alkaline earth metal (e.g., calcium) salt thereof; a graft copolymer of polysaccharide, polyvinylalcohol or gelatin with a monomer of the formula: $CH_2=C(R^1)$-Y, wherein $R^1$ is hydrogen or methyl, and Y is carboxy, nitrile lower-alkoxy-carbonyl or 2-pyrrolidone-1-yl; a cross-linked polysaccharide, a cross-linked polyvinylalcohol, a cross-linked gelatin, a cross-linked polyacrylic acid or an alkali metal salt of said cross-linked polyacrylic acid; and a copolymer of divinylbenzene with a monomer of the formula: $CH_2=C(R^2)$-X, wherein $R^2$ is hydrogen or methyl, and X is carboxy, lower alkoxycarbonyl, lower alkanoyloxy,

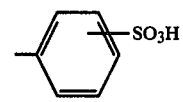

or 2-pyrrolidon-1-yl. Any one of potato starch, corn starch or wheat starch can be used as the polymer material swellable in water of the invention. On the other hand, hydroxymethylcellulose, hydroxypropylcellulose, hydroxypropylstarch, carboxymethylcellulose or its alkaline earth metal salt (e.g., calcium salt) and carboxymethylstarch or its alkaline earth metal salt (e.g., calcium salt) and carboxymethylstarch or its alkaline earth metal salt (e.g., calcium salt) are suitable as the above-mentioned hydroxy-lower alkyl-polysaccharide or carboxy-lower alkyl-polysaccharide. The polysaccharide which can be used to form the graft copolymers thereof with the monomer of the formula (I) may be either starch, cellulose, carboxymethylcellulose or agar. Acrylic acid, methacrylic acid, methyl acrylate, ethyl acrylate, methyl methacrylate, ethyl methacrylate, acrylonitrile and vinylpyrrolidone are suitable as the monomer of the formula (I). Preferred examples of the graft copolymer of said polysaccharide, polyvinylalcohol or gelatin with the monomer of the formula (I) include starch acrylic acid graft copolymer or its alkali metal salt (e.g., sodium, potassium salt), starch.acrylonitrile graft copolymer, starch.methacrylic acid graft copolymer or its alkali metal salt (e.g., sodium, potassium salt), cellulose.acrylic acid graft copolymer or its alkali metal salt (e.g., sodium, potassium salt), cellulose.methacrylic acid graft copolymer or its alkali metal salt (e.g., sodium, potassium salt), cellulose.acrylonitrile graft copolymer, carboxymethylcellulose.methyl acrylate graft copolymer, agar.vinylpyrrolidone graft copolymer, polyvinylalcohol.ethyl acrylate graft copolymer, polyvinylalcohol.acrylic acid graft copolymer or its alkali metal salt (e.g., sodium, potassium salt), and the like. Moreover, starch, cellulose, dextrin, dextran, alkali metal alginate, gum arabic, hydroxy-lower alkyl-starch (e.g., carboxymethylstarch), hydroxy-lower alkyl-cellulose (e.g., hydroxyethylcellulose, hydroxypropylcellulose), lower alkyl-cellulose (e.g., methylcellulose), polyvinylalcohol, gelatin, polyacrylic acid or its alkali metal salt (e.g., sodium or potassium salt) and the like may be used to form the cross-linked compound with a cross-linking agent such as epichlorohydrin, formaldehyde, glutaraldehyde or acrylic acid. Suitable examples of such cross-linked compounds include epichlorohydrin cross-linked carboxymethylcellulose, epichlorohydrin cross-linked carboxymethylstarch or its sodium salt, epichlorohydrin cross-linked hydroxyethylcellulose, epichlorohydrin cross-linked hydroxypropylcellulose, epichlorohydrin cross-linked methylcellulose, epichlorohydrin cross-linked alginic acid, self cross-linked polyacrylic acids or their potassium salts, epichlorohydrin cross-linked dextrin, epichlorohydrin cross-linked dextran, epichlorohydrin cross-linked gum arabic and formaldehyde cross-linked gelatin. Further, acrylic acid, methacrylic acid, metyl acrylate, styrenesulfonic acid, vinyl acetate and vinylpyrrolidone can be suitably used as the monomer of the formula (II). Preferred examples of the copolymer of divinylbenzene with the monomer of the formula (II) are divinylbenzene.acrylic acid copolymer or its alkali metal salt (e.g., sodium, potassium salt), divinylbenzene-methacrylic acid copolymer or its alkali metal salt (e.g., sodium, potassium salt), divinylbenzene.styrenesulfonic acid copolymer or its alkali metal salt (e.g., sodium, potassium salt), divinylbenzene.vinylacetate copolymer, divinylbenzene.methyl acrylate copolymer, divinylbenzene.vinylpyrrolidone copolymer and the like. Among the above-mentioned various polymers, a preferred subgenus of the polymer material swellable in water of the present invention includes starch, crystalline cellulose, agar, alginic acid, or alkali earth metal salts of alginic acid; hydroxy-lower alkyl-cellulose, hydroxy-lower alkyl-starch, carboxy-lower alkyl-cellulose, carboxy-lower alkyl-starch or an alkali earth metal salt thereof; a graft copolymer of starch, cellulose or polyvinylalcohol with a monomer of the formula: $CH_2=C(R^1)-Y'$, wherein $R^1$ is the same as defined above and $Y'$ is carboxy or nitrile; a cross-linked dextrin, a cross-linked dextran, a cross-linked arabic gum, a cross-linked alginic acid, a cross-linked gelatin or a cross-linked polyacrylic acid: and a copolymer of divinylbenzene and a monomer of the formula: $CH_2=C(R^2)-X'$ wherein $R^2$ is hydrogen or methyl and $X'$ is carboxy or

A more preferred subgenus of said polymer material swellable in water of the invention includes, for example, starch, crystalline cellulose, agar, alginic acid or its alkali earth metal salt, hydroxypropylstarch (hydroxypropyl content: 2-7 w/w%), hydroxy-propylcellulose (hydroxypropyl content: 2-7 w/w%), carboxymethylcellulose or its alkaline earth metal salt (e.g., calcium salt), starch.acrylic acid graft copolymer or its alkali metal salt (e.g., sodium, potassium salt), starch.acrylonitrile graft copolymer, cellulose.acrylic acid graft copolymer or its alkali metal salt (e.g., sodium, potassium salt), cellulose.acrylonitrile graft copolymer, polyvinylalcohol.acrylic acid graft copolymer or its alkali metal salt (e.g., sodium, potassium salt), epichlorohydrin cross-linked dextrin, epichlorohydrin cross-linked arabic gum, epichlorohydrin cross-linked dextran, epichlorohydrin cross-linked alginic acid, epichlorohydrin cross-linked polyvinylalcohol, formaldehyde cross-linked gelatin, self cross-linked polyacrylic acid, divinylbenzene.acrylic acid copolymer or its alkali metal salt (e.g., sodium, potassium salt), divinylbenzene.methacrylic acid copolymer or its alkali metal salt (e.g., sodium, potassium salt), divinylbenzene.styrenesulfonic acid copolymer or its alkali metal salt (e.g., sodium, potassium salt) and the like. It is preferred to use such swellable polymer material in the form of fine powder, especially in the form of fine particles having a particle size of about 0.1 to about 300μ. A suitable amount of said polymer material to be incorporated into the core material is about 99 to 3 w/w%, especially about 90 to about 5 w/w%, and more especially about 10 to about 50 w/w%. On the other hand, when said polymer material swellable in water is incorporated into the coating walls of the microcapsules, it is preferred to use said swellable polymer material in an amount of not less than about 0.01 gram, especially about 0.01 to 20 grams, more especially about 0.1 to about 10 grams, per gram of the wall-forming material. When the polymer material swellable in water is incorporated into both of the coating walls and core material of the microcapsules, the amount of said polymer material to be used should also be within the ranges mentioned above.

In making the ethylcellulose microcapsules of the core material, it is preferred to disolve ethylcellulose in cyclohexane at about 80° C., then dispersing the core material therein. Alternatively, when the ethylcellulose microcapsules are prepared by the use of the swellable polymer material-containing core material, it is preferred that a mixture of the core material and the swellable polymer material is granulated into particles having a particle size of about 30 to about 1000μ, especially about 50 to about 500μ, in a conventional manner, and the swellable polymer material-containing core material thus obtained is then dispersed in the ethylcellulose solution at about 80° C. In these cases, it is also preferred that ethylcellulose is dissolved in cyclohexane at a concentration of about 0.5 to about 10 w/v%, especially about one to about 5 w/v%. Moreover, particles of the swellable polymer material-containing core material may be made by treating a mixture of the core material and the swellable polymer material according to either conventional wet-granulation or dry-granulation methods as described in Remington's "Pharmaceutical Science" 13-th Edition, pages 568 to 572 (1965).

When the above-mentioned dispersion is then cooled gradually (e.g., at a rate of 0.05° to 4° C., especially about 0.4° C., per minute), ethylcellulose in the form of "a gel" separates out from the dispersion of about 75° C. thereby depositing on or wrapping the particles of the core material, and the ethylcellulose gel thus deposited forms seamless and complete walls at about 50° C. It is preferred to carry out the phase separation of ethylcellulose under continuous stirring at about 100 to about 600 r.p.m. When the dispersion is then further cooled to a temperature not higher than 40° C. (e.g., 30° to 20° C.), the thus-formed embryonic microcapsules shrink and become solid by solvent loss from the coating walls, thus giving stable ethylcellulose microcapsules. Moreover, said phase-separation of ethylcellulose in cyclohexane may be conducted either in the presence or absence of a phase-separation-inducing agent, i.e., either by coacervation or flocculation of ethylcellulose. If required, in carrying out said phase-separation of ethylcellulose, an organosilicon polymer and/or a surfactant may be used in combination with ethylcellulose. Suitable examples of the phase-separation-inducing agents include polyethylene, butyl rubber, polyisobutylene and polybutadiene. Dimethylpolysiloxane and methylphenylpolysiloxane are suitable as the organosilicon polymer. Further, the surfactants which can be used in the present invention include, for example, an ester of $C_{12-18}$ fatty acid with sorbitan (e.g., sorbitan monolaurate, sorbitan sesquilaurate, sorbitan trilaurate, sorbitan monooleate), an ester of $C_{8-18}$ fatty acid with glycerin (e.g., glycerin monocaprylate, glycerin monolaurate, glycerin monooleate), a phospholipid (e.g., soybean phospholipids, egg-yolk phospholipids), calcium stearoyl-2-lactate, an ester of $C_{8-18}$ fatty acid with propylene glycol (e.g., propylene glycol monocaprylate, propylene glycol monostearate) and an ester of $C_{12-18}$ fatty acid with sucrose (e.g., sucrose mono, di or tri-stearate). It is preferred that said phase-sepration-inducing agent, organosilicon polymer and surfactant are added to the ethylcellulose solution prior to dispersing the core material in said solution. Suitable concentration of the phase-separation-inducing agent, the organosilicon polymer and the surfactant in the ethylcellulose solution is about 0.1 to about 10 w/v%, about 0.01 to about 10 w/v% and about 0.001 to about 10 w/v%, respectively.

Further, in incorporating the swellable polymer material into the coating walls of the ethylcellulose microcapsules, said swellable polymer material may be added to the dispersion either before cooling the dispersion or during the cooling step. Especially, it is preferred that the polymer material swellable in water is added to the dispersion at the stage where coating walls of ethylcellulose in the form of "a gel" are formed on and around the particles of the core material and the coating walls of the thus-obtained embryonic microcapsules have a viscosity of about 0.1 to about 50 P, especially one to 10 P. More specifically, since the coating walls having a viscosity of the above-mentioned range are formed by cooling the dispersion to about 55° to 75° C., especially about 60° to about 70° C., it is preferred that the swellable polymer material is added to the dispersion when cooled to said temperature. By adding the swellable polymer material in the manner as mentioned above, said polymer material can be preferably incorporated or dispersed into the coating walls of the microcapsules. When the dispersion is then further cooled to a temperature not higher than 40° C. (e.g., 30° to 20° C.), the thus-formed embryonic microcapsules shrink and become solid by solvent loss from the coating walls, thus giving stable ethylcellulose microcapsules.

The microcapsules thus obtained may be recovered in the conventional manner such as, for example, decantation, filtration, centrifugation and so forth. In accordance with any one of the methods of the present invention, the ethylcellulose microcapsules can be obtained without being agglomerated into large lumps, each consisting of a myriad of individual capsules. Moreover, if required, the ethylcellulose microcapsules may be washed with cyclohexane, petroleum ether or n-hexane and then dried by conventional means (e.g., hot-air drying method).

Further, the above-mentioned methods of the present invention can be used for microencapsulation of a wide variety of pharmaceutically active compounds or medicaments. Such pharmaceutically active compounds or medicaments which can be used in the present invention include, for example, vitamins, amino acids, peptides, chemotherapeutic agents, antibiotics, agents affecting respiratory organs, antitussive expectorants, antitumor agents, autonomic drugs, neuropsychotropic agents, local anesthetics, muscle relaxants, agents affecting digestive organs, antihistaminic agents, sedatives, anticonvulsants, analgesics, antipyrretic anticoagulants, hepatics, blood sugar-lowering agents and so forth. The medicament to be microencapsulated may also be a composition containing said pharmaceutically active compound togther with an inert excipient or vehicle.

The pharmaceutically active compound-containing ethylcellulose microcapsules of the present invention thus obtained show no substantial retardation in release of said pharmaceutically active compound (core material) in the stomach or other digestive organs because the polymer material swellable in water incorporated into the coating walls and/or core material of the microcapsules effectively accelerates the release of the active ingredient. Namely, when the ethylcellulose microcapsules of the invention are contacted with an aqueous solution such as gastric juice, the polymer material swellable in water which is incorporated into the coating walls and/or core material is swollen rapidly by absorbing water which penetrates into the microcapsules and serves to break the ethylcellulose coating walls or to accelerate the dissolution of the core material in water so as to release rapidly the active ingredient from the core material. Moreover, in the microcapsules of the present invention, the release velocity of a pharmaceutically active compound can be controlled, not only by suitable choice of the water-swellable polymer material and the amount thereof, but also by incorporating said swellable polymer material into either one or both of the coating walls and core material of the microcapsules. For example, when the polymer material swellable in water is incorporated only into the core material, the release of the active ingredient from the microcapsules does not occur until gastric juice penetrates into the core material thereof. However, once gastric juice contacts the core material, the polymer material swellable in water contained therein is swollen by absorbing said gastric juice and accelerates the dissolution of the core material in water, thereby releasing the active ingredient therefrom. On the other hand, if the polymer material swellable in water is incorporated into the coating walls, said ethylcellulose coating walls of the microcapsules when contacted with gastric juice lose their compact network structure and become permeable to water due to the increase in volume of said polymer material, and water thus penetrated into the microcapsules serve to dissolve the core material gradually. Moreover, when said polymer material swellable in water is incorporated into both of the coating walls and core material of the microcapsules, the active ingredient can be released swiftly in stomach because gastric juice first serves to break the ethylcellulose coating walls, and water when contacted with the core material also serves to accelerate the dissolution of the core material. Further, the ethylcellulose microcapsules of the invention which are made by incorporating the swellable polymer material into the coating walls thereof are advantageous in that said swellable polymer material serves to improve the wall characteristics of ethylcellulose film deposited on particles of the core material, and such ethylcellulose microcapsules show excellent free-flowing characteristics. Thus, pharmaceutical preparations such as tablets can be made therefrom without deterioration in the quality of such pharmaceutical preparations.

Practical and presently preferred embodiments of the present invention are illustratively shown in the following Experiments and Examples. Throughout the specification and claims, the terms "lower alkyl", "lower alkoxy" and "lower alkanoyl" should be interpreted as referring to those having one to 4 carbon atoms.

Experiment I

Pyridoxal phosphate-containing microcapsules (a polymer material swellable in water being incorporated into the core material thereof) were prepared according to the following methods. Then, the yield of the microcapsules obtained, the amount of the active ingredient contained in the microcapsules and the $t_{50}$-values thereof (i.e., a period of time which was required to release 50% of the active ingredient from the microcapsules) in water (37° C.) were examined, respectively.

(i) Core materials:

33 parts (by weight) of water were added to a mixture of 80 parts (by weight) of fine powder of pyridoxal phosphate and 20 parts (by weight) of a swellable polymer material shown in the following Table 1, and the mixture was granulated and dried in a conventional manner. The thus-obtained granules having particle size of 105–210μ were used as the core materials in Experiment Nos. 1–16. On the other hand, the core materials (particle size: 105–210μ) in Experiment Nos. 17–20 were prepared from a mixture of 79 parts (by weight) of fine powder of pyridixal phosphate, one part (by weight) of methylcellulose, 20 parts (by weight) of a water-swellable polymer material and 10 parts (by weight) of water in the same manner as described above.

(ii) Preparation of microcapsules:

14 g of ethylcellulose (ethoxy content: 48 w/w %, viscosity: 100 cP) and 21 g of silicone resin (prepared by dispersing 3–15 w/w % of silicon dioxide in 97–95 w/w % of dimethylpolysiloxane having a viscosity of 100–1100 cSt at 25° C.) were dissolved in 700 ml of cyclohexane at 80° C. under stirring. 56 g of the core material were dispersed into the solution, and the mixture was cooled gradually to room temperature (about 25° C.) under stirring at 400 r.p.m. The microcapsules thus formed were recovered by filtration, washed with n-hexane and dried. Then, said microcapsules were passed through JIS (Japanese Industrial Standard) standard sieve (350μ aperture). Pyridoxal phosphate-containing microcapsules which met the requirements of "Pulvers" specified in THE PHARMACOPOEIA OF JAPAN 10th-Edition were obtained.

On the other hand, pyridoxal-containing microcapsules of a control group were prepared in the same manner as described above except that 56 g of pyridoxal phosphate having particle size of 105–210μ were used as the core material.

The results are shown in the following Table 1.

TABLE 1

| Experiment Nos. | polymer materials swellable in water | | Yield (g) of microcapsules | Active ingredient contained in microcapsules (%) | $t_{50}$-** values (hrs) |
|---|---|---|---|---|---|
| | Polymer materials | Degree of Swelling* | | | |
| 1 | Starch.acrylic acid graft fopolymer (sodium salt) | 400 | 61 | 64.8 | 0.4 |
| 2 | Polyvinylalcohol. acrylic acid graft copolymer (sodium salt) | 200 | 67 | 64.2 | 0.6 |
| 3 | Cellulose.acrylic acid graft copolymer (sodium salt) | 700 | 67 | 64.8 | 0.6 |
| 4 | starch.acrylonitrile graft copolymer alkali hydrolysate | 400 | 64 | 64.5 | 0.8 |
| 5 | Cellulose.acrylonitrile graft copolymer alkali hydrolysate | 600 | 61 | 64.5 | 0.8 |
| 6 | Epichlorohydrin cross-linked dextrin | 50 | 67 | 64.3 | 3.2 |
| 7 | Epichlorohydrin cross-linked arabic gum | 100 | 65 | 64.3 | 2.8 |
| 8 | Epichlorohydrin cross-linked polyvinylalcohol | 60 | 63 | 64.6 | 1.2 |
| 9 | Formaldehyde cross-linked gelatin | 20 | 65 | 64.4 | 7.5 |
| 10 | Divinylbenzene.acrylic acid copolymer (sodium salt) | 1000 | 62 | 64.9 | 2.1 |
| 11 | Divinylbenzene.methacrylic acid copolymer (sodium salt) | 240 | 64 | 64.7 | 1.2 |
| 12 | Potato starch | 1.4 | 63 | 64.9 | 16.5 |
| 13 | Epichlorohydrin cross-linked dextran | 35 | 63 | 64.5 | 1.6 |
| 14 | Self cross-linked poly-acrylic acid (sodium salt) | 400 | 64 | 64.0 | 0.4 |
| 15 | Self cross-lined poly-acrylic acid (sodium salt) | 900 | 61 | 64.1 | 0.6 |
| 16 | Carboxymethylcellulose (calcium salt) | 1.9 | 65 | 64.1 | 6.0 |
| 17 | Carboxymethylcellulose | 2.3 | 63 | 64.3 | 5.7 |
| 18 | Sulfonated styrene divinylbenzene copolymer | 1.5 | 61 | 63.7 | 3.5 |

TABLE 1-continued

| Experiment Nos. | polymer materials swellable in water | | Yield (g) of microcapsules | Active ingredient contained in microcapsules (%) | $t_{50}$-** values (hrs) |
| --- | --- | --- | --- | --- | --- |
| | Polymer materials | Degree of Swelling* | | | |
| 19 | (sodium salt) Methacrylic acid divinyl-benzene copolymer (sodium salt) | 1.8 | 64 | 63.5 | 2.9 |
| 20 | Crystalline cellulose | 1.2 | 63 | 64.5 | 23.5 |
| (Control) 21 | — | — | 62 | 86.5 | only 5% of the active ingredient was released after 24 hrs of the experiment. |

Note:
*"Degree of swelling" means the weight (grams) of the water-swellable polymer material which was swollen by immersing one grm of said polymer material in water (37° C.).
*Period of time required to release 50% of the active ingredient from the microcapsules

Experiment II

Trimebutine maleate (Chemical name: 2-dimethylamino-2-phenylbutyl-3,4,5-trimethoxybenzoate hydrogen maleate)-containing microcapsules (a polymer material swellable in water being incorporated into the coating wall thereof) were prepared according to the following methods. Then, the yield of the microcapsules obtained, the amount of the active ingredient (trimebutine maleate) contained in the microcapsules and the $t_{50}$-values thereof (i.e., a period of time which was required to release 50% of the active ingredient from the microcapsules) in water (37°) were examined, respectively.

(i) Core materials:

A solution of 3 parts (by weight) of methylcellulose in 15 parts (by weight) of water was added to a mixture of 23.3 parts (by weight) of trimebutine maleate and 73.7 parts (by weight) of lactose, and the mixture was granulated and dried in a conventional manner. The thus-obtained granules having particle size of 105–350μ were used as the core materials.

(ii) Preparation of microcapsules:

0.8 g of soybean phospholipids and 24 g of silicon resin (prepared by dispersing 3–15 w/w % of silicon dioxide in 97–85 w/w % of dimethylpolysiloxane having a viscosity of 100–1100 cSt at 25° C.) were dissolved in 800 ml of cyclohexane, and 20 g of ethylcellulose (ethoxy content: 48 w/w %, viscosity: 100 cP) were further dissolved therein at 80° C. 100 g of the core material were dispersed in the solution, and the mixture was cooled gradually under stirring at about 400 r.p.m. When the mixture was cooled to about 65° C., 100 g of fine powder of a polymer material swellable in water was added thereto in the form of a fine powder. Then, the mixture was further cooled to room temperature under the same conditions as above. The microcapsules thus formed were recovered by filtration, washed with n-hexane and dried. The microcapsules were passed through JIS standard sieve (500μ aperture) and then JIS standard sieve (105μ). The microcapsules which passed through the former sieve but did not pass through the latter sieve were collected. Trimebutine maleate-containing microcapsules which met the requirements of "Fine Granules" specified in THE PHARMACOPOEIA OF JAPAN 10th-Edition were obtained.

Trimebutine maleate-containing microcapsules of a control group were prepared in the same manner as described above but without using said swellable polymer material. The results are shown in the following Table 2.

TABLE 2

| Experiment Nos. | polymer materials swellable in water | | Yield (g) of microcapsules | Active ingredient contained in microcapsules (%) | $t_{50}$- values (hrs) |
| --- | --- | --- | --- | --- | --- |
| | Polymer materials | Degree of Swelling* | | | |
| 1 | Carboxymethylcellulose (calcium salt) | 1.9 | 208 | 10.8 | 8 |
| 2 | Carboxymethylcellulose | 2.3 | 203 | 10.9 | 7 |
| 3 | Corn starch | 1.3 | 204 | 11.2 | 24 |
| 4 | Potato starch | 1.4 | 204 | 10.6 | 20 |
| 5 | Hydroxypropyl starch | 1.3 | 206 | 10.7 | 26 |
| 6 | Epichlorohydrin cross-linked dextran | 35 | 205 | 10.5 | 5 |
| 7 | Epichlorohydrin cross-linked polyvinylalcohol | 60 | 209 | 11.1 | 4 |
| 8 | Hydroxypropyl cellulose | 20 | 207 | 10.7 | 11 |
| 9 | Agar | 4.4 | 209 | 11.0 | 9 |
| (Control) 10 | — | — | 101 | 19.9 | 78 |

Note:
*same as defined in the footnote of Table 1.

Experiment III

Pyridoxal phosphate-containing microcapsules (a polymer material swellable in water being incorporated into both of the core material and coating wall thereof) were prepared according to the following methods. Then, the yield of the microcapsules obtained, the amount of the active ingredient contained in the microcapsules and the $t_{50}$-values thereof (i.e., a period of time which was required to release 50% of the active ingredient from the microcapsules) in water (37° C.) were examined, respectively.

(i) Core materials:

25 parts (by weight) of water were added to a mixture of 90 parts (by weight) of fine powder of pyridoxal phosphate and 10 parts (by weight) of self cross-linked polacrylic acid (Degree of Swelling: 400), and the mixture was granulated and dried in a conventional manner. The thus-obtained granules having particle size of 105–210 were used as the core materials.

(ii) Preparation of microcapsules:

24 g of a phase separation-inducing agent shown in the following Table 3 were dissolved in 800 ml of cyclohexane, and 16 g of ethylcellulose (ethoxy content: 49 w/w%, viscosity: 90 cP) were further dissolved therein at 80° C. 64 g of the core material were dispersed in the solution, and the mixture was cooled gradually under stirring at 400 r.p.m. When the mixture was cooled to about 65° C., 80 g of the calcium salt of carboxymethylcellulose (degree of swelling: 1.9) were added thereto. Then, the mixture was cooled to room temperature under the same conditions as above. The microcapsules thus formed were recovered by filtration, washed with n-hexane and dried. The microcapsules were passed through JIS standard sieve (350μ aperture). Pyridoxal phosphate-containing microcapsules which met the requirements of "Pulvers" specified in THE PHARMACOPOEIA OF JAPAN 10th-Edition were obtained.

The results are shown in the following Table 3.

TABLE 3

| Experiment Nos. | Phase separation-inducing agents | Yield (g) of microcapsules | Active ingredient contained in microcapsules (%) | $t_{50}$-values (minutes) |
|---|---|---|---|---|
| 1 | Polyisobutyrene (molecular weight: 800,000) | 156 | 36.3 | 57 |
| 2 | Polyethylene (molecular weight: 7,000) | 152 | 36.9 | 33 |
| 3 | Silicon resin* | 153 | 36.5 | 65 |
| 4 | Butyl rubber (viscosity of 67 "Mooney" 8 minutes reading at 100° C.) | 155 | 36.7 | 41 |
| 5 | Dimethyl polysiloxane (viscosity at 25° C., 500,000 cSt) | 157 | 36.7 | 69 |

Note:
*same as used in Experiment I.

EXAMPLE 1

0.4 g of soybean phospholipids and 24 g of silicon resin (same one as used in Experiment II) were dissolved in 800 ml of cyclohexane, and 20 g of ethylcellulose (same one as used in Experiment I) were dissolved therein at 80° C. 60 g of timepidium bromide (Chemical name: di-(2-thienyl)-N-methyl-5-methoxy-3-piperidilidene)methane methyl bromide) having particles size of 88–210μ were dispersed in the solution, and the mixture was cooled gradually under stirring at 400 r.p.m. When the mixture was cooled to 65° C., 100 g of carboxymethylcellulose were added thereto. Then, the mixture was cooled to room temperature under the same conditions as above. The microcapsules thus formed were recovered by filtration, washed with n-hexane and dried. Then, the microcapsules were passed through JIS standard sieve (350μ aperture). 176 g of timepidium bromide-containing microcapsules which met the requirements of "Pulvers" specified in THE PHARMACOPOEIA OF JAPAN 10th-Edition were obtained.

EXAMPLE 2

232 g of timepidum bromide-containing microcapsules were obtained in the same manner as described in Example 1 except that 160 g of wheat starch were used instead of carboxymethylcellulose (calcium salt).

EXAMPLE 3

(1) 7 parts (by weight) of aqueous 45 v/v% ethanol were added to a mixture of 13.3 parts (by weight) of diltiazem hydrochloride, 41.7 parts (by weight) of corn starch, 40 parts (by weight) of lactose and 5 parts (by weight) of dextrin, and the mixture was granulated and dried in a conventional manner. The thus-obtained granules having particle size of 105–250μ were used as the core material.

(2) 0.4 g of calcium stearyl-lactate (Chemical name: calcium stearoyl-2-lactate) and 24 g of silicon resin (same one as used in Experiment I) were dissolved in 800 ml of cyclohexane, and 16 g of ethylcellulose (same one as used in Experiment I) were dissolved therein at 80° C. 80 g of the core material were dispersed in the solution, and the mixture was cooled gradually under stirring at about 400 r.p.m. When the mixture was cooled to about 65° C., 80 g of carboxymethylcellulose and 80 g of corn starch were added thereto. Then, the mixture was cooled to room temperature under the same conditions as above. The microcapsules thus formed were recovered by filtration, washed with n-hexane and dried. The mcrocapsules were passed through JIS standard sieve (350μ aperture). 250 g of diltiazem hydrochloride-containing microcapsules which met the requirements of "Pulvers" specified in THE PHARMACOPOEIA OF JAPAN 10th-Edition were obtained.

EXAMPLE 4

249 g of diltiazem hydrochloride-containing microcapsules were obtained in the same manner as described in Example 3 except that 80 g of agar and 80 g of hydroxypropyl-starch were used instead of carboxy methylcellulose and corn starch.

What we claim is:

1. In ethylcellulose microcapsules comprising (i) particles of a core material and (ii) ethylcellulose coating walls deposited on and around said particles of the core material, the improvement wherein a polymer material which shows at least 1.2 times increase in weight by immersing it in water at 37° C. is incorporated into the ethylcellulose coating walls and/or the core material of the microcapsules, said polymer material being taken from the class consisting of agar, hydroxypropyl-cellulose having a hydroxypropoxy content of 2-7 w/w %, free carboxymethylcellulose or its alkaline earth metal salt, starch.acrylic acid graft copolymer or its alkali metal salt, starch.acrylonitrile graft copolymer, cellulose.acrylic acid graft copolymer or its alkali metal salt, cellulose.acrylonitrile graft copolymer, polyvinylalcohol.acrylic acid graft copolymer or its alkali metal salt, epichlorohydrin cross-linked dextrin, epichlorohydrin cross-linked gum arabic, epichlorohydrin cross-linked dextran, epichlorohydrin cross-linked polyvinylalcohol, formaldehyde cross-linked gelatin, acrylic acid cross-linked polyacrylic acid, divinylbenzene acrylic acid copolymer or its alkali metal salt, divinylbenzene methacrylic acid copolymer or its alkali metal salt and divinylbenzene styrenesulfonic acid copolymer or its alkali metal salt.

2. The microcapsules of claim 1 wherein said ethylcellulose has an ethoxy content of 46.5 to 55.0 w/w% and is present in an amount of 0.01 to 10.0 grams per gram of core material, there being at least 0.01 grams of said polymer material per gram of said ethylcellulose.

3. The microcapsules of claim 1 wherein there is 0.01 to 20 grams of said polymer material per gram of said ethylcellulose.

4. The microcapsules of claim 1 wherein the core material comprises a pharmaceutically active compound having a particle size of 30–1000μ, ethylcellulose having an ethoxy content of 46.5 to 55 w/w % and a viscosity (measured at 25° C. with respect to a 5 w/w % solution of it in tolueneethanol (4:1)) of 3 to 500 cP is used in an amount of 0.01 to 10 grams per gram of the core material, and the polymer material having a particle size of 0.1 to 300μ is used in an amount of 0.01 to 20 grams per gram of ethylcellulose.

5. The microcapsules of any one of claims 1 to 4 wherein at least one member selected from the group consisting of a phase-separation-inducing agent, an organosilicon polymer and a surfactant is further added to the solution of ethylcellulose.

6. A process for preparing ethylcellulose microcapsules, which comprises the steps of:
   (i) dissolving ethylcellulose in cyclohexane to form a solution,
   (ii) dispersing particles of a core material in said solution,
   (iii) cooling the dispersion in the presence of a polymer material until ethylcellulose separates out from the dispersion to form coating walls on and around the particles of the core material, said polymer material showing at least 1.2 times increase in weight when immersed in water at 37° C. and being selected from the class consisting of agar, hydroxypropyl-cellulose having a hydroxypropoxy content of 2–7 w/w %, free carboxymethylcellulose or its alkaline earth metal salt, starch.acrylic acid graft copolymer or its alkali metal salt, starch.acrylonitrile graft copolymer, cellulose.acrylic acid graft copolymer or its alkali metal salt, cellulose.acrylonitrile graft copolymer, polyvinylalcohol.acrylic acid graft copolymer or its alkali metal salt, epichlorohydrin cross-linked dextrin, epichlorohydrin cross-linked gum arabic, epichlorohydrin cross-linked dextran, epichlorohydrin cross-linked polyvinylalcohol, formaldehyde cross-linked gelatin, acrylic acid-cross-linked polyacrylic acid, divinylbenzene.acrylic acid copolymer or its alkali metal salt, divinylbenzene methacrylic acid copolymer or its alkali metal salt, and divinylbenzene.styrenesulfonic acid copolymer or its alkali metal salt, and
   (iv) recovering the resultant microcapsules therefrom.

7. The process according to claim 6, wherein ethylcellulose having an ethoxy content of 46.5 to 55 w/w % is used in an amount of 0.01 to 10 grams per gram of the core material, and the polymer material is used in an amount of not less than 0.1 gram per gram of ethylcellulose.

8. The process according to claim 6, wherein the polymer material is used in an amount of 0.01 to 20 grams per gram of ethylcellulose.

9. The process according to claim 6, wherein the core material comprises a pharmaceutically active compound having a particle size of 30–1000μ, ethylcellulose having an ethoxy content of 46.5 to 55 w/w % and a viscosity (measured at 25° C. with respect to a 5 w/w % solution of it in toluene-ethanol (4:1)) of 3 to 500 cP is used in an amount of 0.01 to 10 grams per gram of the core material, and the polymer material having a particle size of 0.1 to 300μ is used in an amount of 0.001 to 20 grams per gram of ethylcellulose.

10. The process according to any one of claims 6–9, wherein at least one member selected from the group consisting of a phase-separating-inducing agent, an organosilicon polymer and a surfactant is further added to the solution of ethylcellulose.

11. A process for preparing ethylcellulose microcapsules, which comprises the steps of:
   (i) dissolving ethylcellulose in cyclohexane to form a solution,
   (ii) dispersing particles of a polymer material-containing core material in said solution, said polymer material showing at least 1.2 times increase in weight when immersed in water at 37° C. and being selected from the class consisting of agar, hydroxypropylcellulose having a hydroxypropoxy content of 2-7 w/w %, free carboxymethylcellulose or its alkaline earth metal salt, starch.acrylic acid graft copolymer or its alkali metal salt, starch-acrylonitrile graft copolymer, cellulose.acrylic acid graft copolymer or its alkali metal salt, cellulose.acrylonitrile graft copolymer, polyvinylalcohol.acrylic acid graft copolymer or its alkali metal salt, epichlorohydrin cross-linked dextrin, epichlorohydrin cross-linked gum arabic, epichlorohydrin cross-linked dextran, epichlorohydrin cross-linked polyvinylalcohol, formaldehyde cross-linked gelatin, acrylic acid.cross-linked polyacrylic acid, divinylbenzene.acrylic acid copolymer or its alkali metal salt, divinylbenzene.methacrylic acid copolymer or its alkali metal salt, and divinylbenzene.styrenesulfonic acid copolymer or its alkali metal salt,
   (iii) cooling the dispersion until ethylcellulose separates out from the dispersion to form coating walls on and around the core material, and
   (iv) recovering the resultant microcapsules therefrom.

12. The process according to claim 11, wherein the dispersion is cooled in the presence of a polymer material which shows at least 1.2 times increase in weight when immersed in water at 37° C. and which is selected from the class consisting of agar, hydroxypropylcellulose having a hydroxypropoxy content of 2–7 w/w %, free carboxymethylcellulose or its alkaline earth metal salt, starch.acrylic acid graft copolymer or its alkali metal salt, starch.acrylonitrile graft copolymer, cellulose.acrylic acid graft copolymer or its alkali metal salt, cellulose.acrylonitrile graft copolymer, epichlorohydrin cross-linked dextrin, epichlorohydrin cross-linked gum arabic, epichlorohydrin cross-linked dextran, epichlorohydrin cross-linked polyvinylalcohol, formaldehyde cross-linked gelatin, acrylic acid.cross-linked polyacrylic acid, divinylbenzene acrylic.acid copolymer or its alkali metal salt, divinylbenene.methacrylic acid copolymer or its alkali metal salt and divinylbenzene.styrenesulfonic acid copolymer or its alkali metal salt.

13. The process according to claim 11 or 12, wherein ethylcellulose having an ethoxy content of 46.5 to 55 w/w % is used in an amount of 0.01 to 10 grams per gram of the core material, and the amount of the polymer material incorporated into the core material is 3 to 99 w/w %.

14. The process according to claim 11 or 12, wherein the dispersion is cooled in the presence of not less than 0.01 gram of the polymer material per gram of said ethylcellulose.

15. The process according to claim 11 or 12, wherein the dispersion is cooled in the presence of 0.01 to 20 grams of the polymer material per gram of ethylcellulose.

16. The process according to claim 11 or 12, wherein the core material is a pharmaceutically active compound having a particle size of 30-100μ, ethylcellulose having an ethoxy content of 46.5 to 55 w/w % and a viscosity, measured at 25° C. with respect to a 5 w/w % solution in toluene-ethanol (4:1), of 3 to 500 cP is used in an amount of 0.01 to 10 grams per gram of the core material.

17. The process according to claim 11 or 12 wherein at least one member selected from the group consisting of a phase-separation-inducing agent, an orgnosilicon polymer, and a surfactant is added to the solution of ethylcelullose.

* * * * *